United States Patent [19]

Cevasco

[11] Patent Number: 4,996,350

[45] Date of Patent: Feb. 26, 1991

[54] METHOD FOR THE PREPARATION OF DIALKYL DICHLOROSUCCINATES

[75] Inventor: Albert A. Cevasco, Belle Mead, N.J.

[73] Assignee: American Cyanamid Company, Stamford, Conn.

[21] Appl. No.: 483,917

[22] Filed: Nov. 17, 1989

Related U.S. Application Data

[63] Continuation of Ser. No. 101,454, Oct. 1, 1987, abandoned.

[51] Int. Cl.$^5$ .................... C07C 67/307; C07C 69/63
[52] U.S. Cl. .................................. 560/192; 546/170; 546/184; 548/400; 560/44
[58] Field of Search ........................................ 560/192

[56] References Cited

FOREIGN PATENT DOCUMENTS 46-21564  6/1971  Japan .................................. 560/192

Primary Examiner—Vivian Garner
Attorney, Agent, or Firm—Carmella A. O'Gorman

[57] ABSTRACT

The present invention relates to an improved method for the preparation of dialkyl dichlorosuccinates by chlorination of a dialkyl maleate in the presence of a catalytic amount of a $C_1-C_4$ alkyl alcohol in the absence of a solvent which are useful intermediates in the preparation of anilinofumarates. Anilinofumarates are, in turn, used in the preparation of 2-(2-imidazolin-2-yl)quinoline-3-carboxylic acid herbicidal agents.

6 Claims, No Drawings

METHOD FOR THE PREPARATION OF DIALKYL DICHLOROSUCCINATES

This application is a continuation of copending application Ser. No. 07/101,454, filed Oct. 1, 1987, now abandoned.

BACKGROUND OF THE INVENTION

The present invention relates to novel methods for preparing precursors for quinoline-2,3-dicarboxylic acids. These acids are useful intermediates in the preparation of herbicidal pyridine and quinoline imidazolinone herbicidal compounds.

The herbicidal pyridine and quinoline imidazolinone compounds prepared from the present compounds include 2-(4-isopropyl-4-methyl-5-oxo-2-imidazolin-2-yl)quinoline-3-carboxylic acid, and esters and salts thereof and are disclosed in U.S. Pat. No. 4,638,068, incorporated herein by reference. These herbicidal imidazolinyl quinolinecarboxylic acids may be prepared by the procedure described in U.S. Pat. No. 4,518,780 (incorporated herein by reference) by cyclization, under basic conditions, with an appropriately substituted 2-carbamoyl quinoline-3-carboxylic acid, that, in turn, is prepared by the reaction of a substituted quinoline-2,3-dicarboxylic acid anhydride and appropriately substituted aminocarboxamide or aminothiocarboxamide. Quinoline-2,3-dicarboxylic acid anhydrides are readily prepared from the diacids by procedures well known in the art. However, the diacids themselves are not readily available.

Pending application for United States Letters Patent of Robert Doehner, Ser. No. 698,192 filed Feb. 4, 1985 now U.S. Pat. No. 4,656,283, describes a method useful for the preparation of quinoline-2,3-dicarboxylic acid and esters thereof by reacting a beta-anilino-alpha,-betaunsaturated ester with an immonium salt (commonly called a Vilsmeier reagent). The beta-anilino-alpha, beta-unsaturated esters are obtained by the reaction of appropriately substituted anilines with ketoesters or dialkyl acetylene dicarboxylates. The overall reaction for the preparation of quinoline-2,3-dicarboxylates is illustrated in Flow Diagram I.

FLOW DIAGRAM I

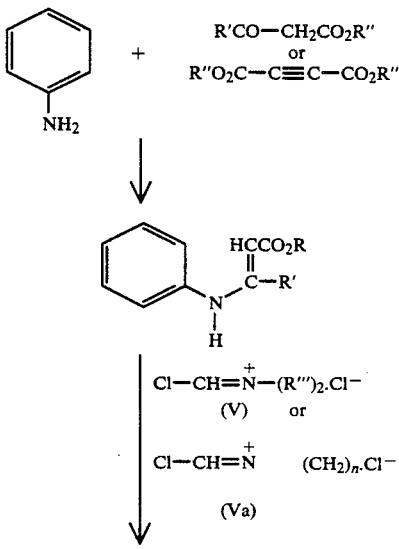

-continued
FLOW DIAGRAM I

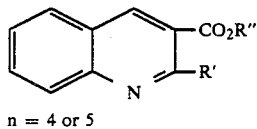

n = 4 or 5 wherein R' is $CH_3$ or $CO_2R''$ and R'' is $C_1$-$C_4$ alkyl, and R''' is $CH_3$ or $C_1$-$C_4$ alkyl.

Where R' is $CH_3$, the diacid is obtained by concurrent oxidation and hydrolysis of the product under aqueous basic conditions in the presence of nickel peroxide, as described in U.S. Pat. No. 4,459,409 (incorporated herein by reference).

Unfortunately, the availability of ketoesters and dialkyl acetylene dicarboxylates, such as diethyloxalacetate and diethyl acetylenedicarboxylate, is limited, thus restricting the quantities of anilinofumarate and quinoline-2,3-dicarboxylic acid, the intermediates required for preparing herbicidal 2-(4-isopropyl-4-methyl-5-oxo-2-imidazolin-2-yl)quinoline- 3-carboxylic acid, esters and salts thereof.

U.S. Pat. No. 4,675,432, incorporated herein by reference, describes a method for the preparation of anilinofumarates in which dichlorosuccinates are reacted with aniline in an organic solvent in the presence of aqueous base and a phase transfer catalyst in a temperature in the range of 20° C. to 90° C. for one to 24 hours.

Pending Application for United States Letters Patent of D. Maulding, Ser. No. 902,275, filed Aug. 29, 1986, now U.S. Pat. No. 4,766,218, describes a method for the preparation of anilinofumarates by the reaction of dichlorosuccinates with specific amines and the subsequent displacement of the amine with aniline in the presence of an organic acid.

U.S. Pat. No. 2,527,345 describes a method for the preparation of dialkyl dichlorosuccinates by introducing a stream of chlorine in intimate contact with a liquid dialkyl maleate maintained at a temperature of 25° C. to 125° C., at a sufficiently high rate to permit a portion of the chlorine gas to pass through the reaction mixture unreacted, in the presence of a chlorination catalyst such as ferric chloride, phosphorus pentoxide or sulfur monochloride.

Japanese patent application 71,21,564 describes an improved method for the preparation of dialkyl dichlorosuccinates by adding chlorine to a dialkyl maleate in a chlorinated hydrocarbon solvent in the presence of an alcohol, the reactions being, in general, conducted at low temperatures and in the dark.

It is an object of the present invention to provide an improved method for the preparation of dialkyl dichlorosuccinates which results in increased productivity and shorter reaction times.

SUMMARY OF THE INVENTION

The present invention provides an improved method for the preparation of dialkyl dichlorosuccinates resulting in significantly increased productivity and reduction in reaction times. In the process of the present invention, dialkylmaleate is reacted with chlorine, in the absence of a solvent, but in the presence of a catalytic quantity of an alcohol, at a temperature range of about 20° C. to about 75° C., for a sufficient period of time to complete the reaction.

The improved process of this invention provides yields of about 80% to 90% pure dialkyl dichlorosuccinates directly, without the use of a solvent. The dialkyl dichlorosuccinates obtained by the method of this invention may be reacted directly with aniline and a minimum of two molar equivalents of aqueous base in the presence of a phase transfer catalyst to yield anilinofumarates by the procedures described in U.S. Pat. No. 4,675,432, without further purification.

Additionally, since the method of this invention does not employ a chlorinated hydrocarbon solvent, it reduces handling, effluent and processing steps associated with solvent recovery.

DETAILED DESCRIPTION OF THE INVENTION

The present invention provides an improved method for the preparation of dialkyl dichlorosuccinates, said method comprising reacting a dialkyl maleate of formula I $$\begin{array}{c} HC-CO_2R_1 \\ \parallel \\ HC-CO_2R_1 \end{array} \quad (I)$$

wherein $R_1$ is $C_1$–$C_4$ alkyl with 1.0 to 1.5 molar equivalents of chlorine in the presence of 2.5% to 15% of a $C_1$–$C_4$ alkyl alcohol at a temperature range of about 20° C. to 75° C., preferably 25° C. to 60° C., for one to five hours.

In accordance with the method of this invention, chlorine gas (150.0 g, 2.12 moles) uniformly is added over two hours to a diethyl maleate (350 0 g, 98% purity, 2.0 moles) and anhydrous ethyl alcohol (9.0 g, 0.2 mole). The temperature of the reaction solution is maintained at 20° C. to 35° C. with external cooling. The solution is stirred for an additional two hours at 25° C. to 40° C., followed by a nitrogen sparge for one hour at 40° C. to 50° C. to remove excess chlorine to yield 492 g (90%) of diethyl dichlorosuccinate (88.5% pure).

The invention is further illustrated by the following non-limiting examples.

EXAMPLES 1–8

Chlorine gas is added uniformly at various rates to diethyl maleate containing 10 to 15 mol percent of an ethanol, and the resulting reaction mixture is allowed to stir for various periods of time. The resulting mixture is sparged with nitrogen to give the yields of diethyl dichlorosuccinate listed in Table I below.

TABLE I

| Example | Diethyl maleate g | Purity | mols | Ethanol mols | Chlorine mols | Chlorine Feed rate g/min | Temp °C. | Chlorine addition min | Hold hr | % Yield diethyl dichlorosuccinate |
|---|---|---|---|---|---|---|---|---|---|---|
| 1 | 17.5 | 99.0 | 0.1 | 0.015 | .10 | 0.16 | 20–32 | 50 | 3.0 | 87.3 |
| 2 | 35.0 | 99.0 | 0.201 | 0.02 | .22 | 0.12 | 25–32 | 125 | 2.0 | 89.1 |
| 3 | 350.0 | 99.0 | 2.01 | 0.2 | 2.12 | 1.25 | 22–32 | 120 | 2.0 | 89.7 |
| 4 | 400.0 | 96.0 | 2.23 | 0.2 | 2.42 | 1.63 | 23–37 | 105 | 2.5 | |
| 5 | 225.0 | 78.4 | 1.02 | 0.13 | 1.19 | 0.94 | 23–32 | 90 | 1.75 | 94.1 |
| 6 | 1156.4 | 95.7 | 6.428 | 0.64 | 6.79 | 3.21 | 25–40 | 150 | 2.25 | — |
| 7 | 483.8 | 94.9 | 2.67 | 0.27 | 2.95 | 1.61 | 25–34 | 130 | 2.0 | 92.5 |
| 8 | 513.3 | 96.0 | 2.86 | 0.3 | 3.8 | 1.92 | 15–35 | 140 | 16.0 | 88.1 |

What is claimed is:

1. A method for the preparation of dialkyl dichlorosuccinates, said method consisting essentially of reacting dialkyl maleate with chlorine in the presence of a catalytic amount of a $C_1$–$C_4$ alkyl alcohol at a temperature range of about 20° C. to 75° C. for sufficient period of time to complete said reaction.

2. A method according to claim 1, wherein said chlorine is present at 1.0 to 1.5 molar equivalents.

3. A method according to claim 2, wherein said time is one to five hours.

4. A method according to claim 3, wherein said alcohol is 2.5% to 15%.

5. A method according to claim 5, wherein said alcohol is ethanol.

6. A method according to claim 5, wherein said temperature is 25° C. to 60° C.

* * * * *

UNITED STATES PATENT AND TRADEMARK OFFICE
CERTIFICATE OF CORRECTION

PATENT NO. : 4,996,350

DATED : February 26, 1991

INVENTOR(S) : Albert A. Cevasco

It is certified that error appears in the above-identified patent and that said Letters Patent is hereby corrected as shown below:

On the title apge, item no. 21, Appl. No. "483,917" should be replaced with --438,917--.
In claim 5, col. 4, line 46, the reference to "claim 5" should read --claim 4--.

Signed and Sealed this

Fifth Day of May, 1992

*Attest:*

DOUGLAS B. COMER

*Attesting Officer*   *Acting Commissioner of Patents and Trademarks*